US00PP15892P2

(12) United States Plant Patent
Read

(10) Patent No.: US PP15,892 P2
(45) Date of Patent: Jul. 26, 2005

(54) ***GAILLARDIA* PLANT NAMED 'FANFARE'**

(50) Latin Name: *Gaillardia×grandiflora*
Varietal Denomination: Fanfare

(76) Inventor: Richard Read, 32 Craigweil Lane. Aldwick, Bognor Regis, PO21 4AN (GB)

( * ) Notice: Subject to any disclaimer, the term of this patent is extended or adjusted under 35 U.S.C. 154(b) by 19 days.

(21) Appl. No.: 10/293,191

(22) Filed: Nov. 12, 2002

(51) Int. Cl.[7] ..... A01H 5/00
(52) U.S. Cl. ..... Plt./263
(58) Field of Search ..... Plt./263

(56) References Cited
PUBLICATIONS
UPOV ROM GTITM Computer Database GTI Jouve Retrieval Software 2003/04 Citation for 'Fanfare'.*
* cited by examiner

*Primary Examiner*—Kent Bell
*Assistant Examiner*—W C Haas

(57) ABSTRACT

A new cultivar of *Gaillardia* named 'Fanfare' that is distinguishable by a long blooming period, gray-green leaves, a compact, low-growing habit and large fragrant daisy-like inflorescences composed of brilliant yellow-orange colored tubular ray flowers with red coloration to the outside and inside of each corolla. In combination these traits set 'Fanfare' apart from all other existing varieties of *Gaillardia* known to the inventor.

2 Drawing Sheets

Botanical designation: Genus: *Gaillardia*. Species: ×*grandiflora*.
Denomination: Fanfare.

BACKGROUND OF THE INVENTION

The present invention relates to a new and distinct cultivar of blanket flower, an herbaceous perennial that is grown for use as an ornamental landscape and container plant. The new invention is known botanically as *Gaillardia×grandiflora* and will be referred to hereinafter by the cultivar name 'Fanfare'. *Gaillardia* is in the family Compositae, under which the commonly referred to "flower" is actually the inflorescence, and made up of smaller ray flowers and disc florets. The ray flowers themselves have the appearance of "petals".

'Fanfare' is a chance seedling that was discovered and isolated as a single plant by the inventor in 1997 in a cultivated area of West Sussex, England. The invention had grown from commercially available seed a selection of annual and perennial plants, including *Gaillardia* 'Goblin' (unpatented) for a garden display in 1996 and 1997. The inventor found amongst these plants two seedlings of *Gaillardia* that appeared substantially different in character and flower form from any variety of *Gaillardia* known to the inventor. The two seedlings were similar in appearance, except that one, the subject of this application and named by the inventor as 'Fanfare', was approximately 25% shorter in height that the other seedling. The second, taller, seedling was destroyed. The parents of 'Fanfare' are presumed to be *Gaillardia* 'Goblin' (unpatented). The female parent plant is presumed to be *Gaillardia* 'Goblin' and the male parent plant is presumed to be *Gaillardia* 'Goblin'. 'Fanfare' differs from the parent plant in its ray flowers, which are each tubular in shape and terminate in four petals.

'Fanfare' spreads slightly and exhibits a compact, low-growing habit with large fragrant daisy-like inflorescences that are brilliant yellow-orange in color. The ray flowers of 'Fanfare' are tubular, and the plant is floriferous, flowering over a long period of time. Cultural requirements include full sun, moderate water and well draining soil such as loam. Hardiness is classified as USDA Zone 5.

The distinguishing characteristics of 'Fanfare' are flower color, shape of ray flowers, plant habit, and abundance of flowers over a long blooming period. The closest comparison plants are *Gaillardia* 'Goblin' (not patented) and *Gaillardia* 'Dazzler' (not patented). 'Fanfare' is distinguishable from 'Goblin' by tubular ray flowers, longer stems, and a larger center area of disc florets on the inflorescence. 'Fanfare' is distinguishable from 'Dazzler' by plant height, being approximately half the height of 'Dazzler'.

The first asexual reproduction of 'Fanfare' was accomplished in 1998 by the inventor in a cultivated area of West Sussex, England. The method used was softwood cuttings. Since that time subsequent generations have been determined stable and true to type.

SUMMARY OF THE INVENTION

The following traits have been repeatedly observed and represent the distinguishing characteristics of Fanfare. These traits in combination distinguish 'Fanfare' from all other existing varieties of *Gaillardia×grandiflora* known to the inventor. 'Fanfare' has not been tested under all possible conditions and phenotypic differences may be observed with variations in environmental, climatic, and cultural conditions, however, without any variance in genotype.

1. 'Fanfare' is slightly spreading and exhibits a compact habit.
2. 'Fanfare' is an herbaceous perennial.
3. 'Fanfare' exhibits large fragrant daisy-like inflorescences composed of numerous tubular ray flowers.
4. 'Fanfare' exhibits elongated gray-green leaves.
5. 'Fanfare' is 350 mm. in height and 450 mm. in width at maturity.
6. The tubular ray flowers in each inflorescence are brilliant yellow-orange in color with red coloration to the outside and inside of the corolla tube.
7. 'Fanfare' is hardy to USDA Zone 5.

BRIEF DESCRIPTION OF THE DRAWINGS

The accompanying color drawings illustrate the overall appearance of the new *Gaillardia* cultivar 'Fanfare' showing the colors as true as is reasonably possible to obtain in colored reproductions of this type. Colors in the photographs may differ from the color values cited in the detailed botanical description, which more accurately describes the actual colors of the new 'Fanfare'.

The Drawing labeled as FIG. 1 depicts two plants of 'Fanfare' established in a test bed at the University of Michigan, Lansing, Mich., and photographed in July 2004. The plants in the Drawing are approximately one year old from a cutting.

Figure 1:
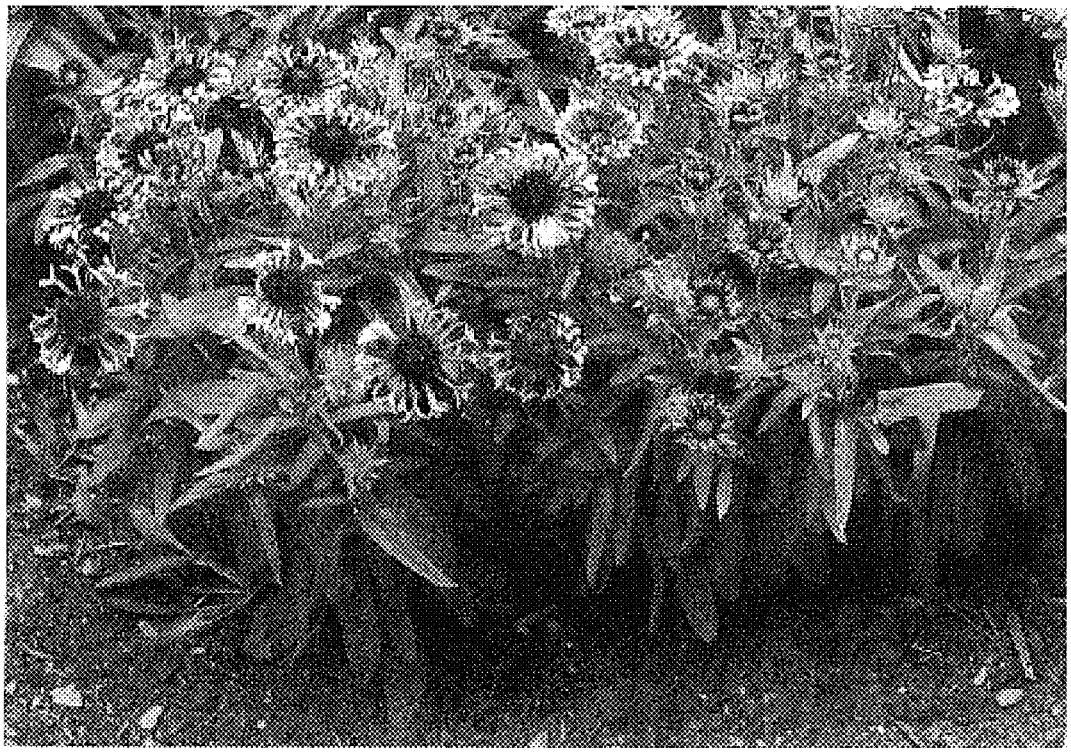
Figure 2:
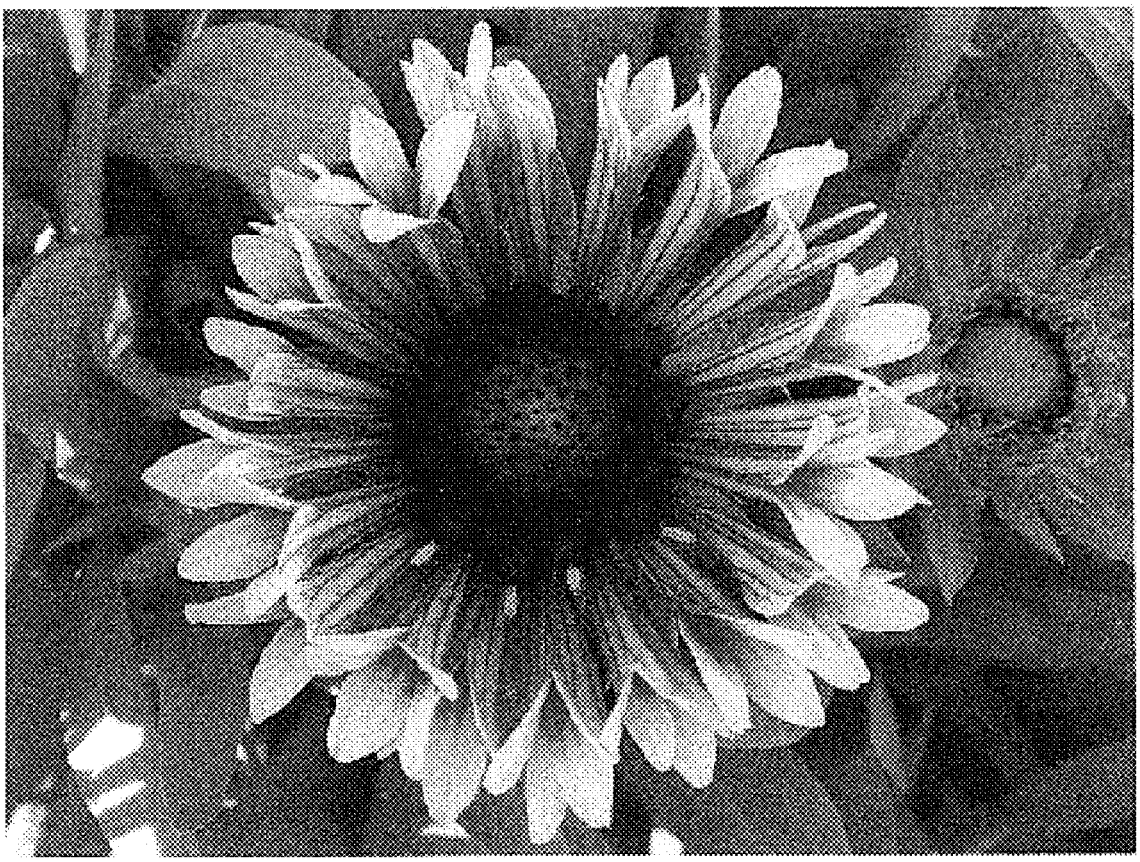

The Drawing labeled as FIG. 2 depicts a close-up view of a single inflorescence of 'Fanfare' and showing the numerous tubular yellow-orange ray flowers with bright red inner and outer corolla tubes.

The Drawings were made by printing onto semi-gloss proprietary ink-jet photographic paper images taken with a digital camera and although flower and foliage colors may appear different from actual colors due to light reflectance, they are as accurate as possible by such means.

BOTANICAL DESCRIPTION OF THE PLANT

The following is a detailed botanical description of the new *Gaillardia×grandiflora* cultivar 'Fanfare'. Observations, measurements, values and comparisons were compiled in Arroyo Grande, Calif. from 2-month-old plants in 15-centimeter containers. The plants were grown inside a glass greenhouse then moved to a retractable roof house. Color determinations are made in accordance with The 2001 Royal Horticultural Society Colour Chart from London England, except where general color terms of ordinary dictionary significant are used.

Botanical classification: *Gaillardia×grandiflora.*
Genus: *Gaillardia.*
Species: *×grandiflora.*
Common name: Blanket flower.
Parentage: *Gaillardia×grandiflora* 'Fanfare' is a chance seedling that resulted from the open pollination of the following presumed parent plants:
*Presumed female parent.*—*Gaillardia* 'Goblin'.
*Presumed male parent.*—*Gaillardia* 'Goblin'.
Propagation method: Softwood cuttings.
Rooting system: Fine and fibrous.
Vigor: Moderate vigor.
Time to develop roots: 14 to 20 days are needed for an initial cutting to develop roots.
Temperature to develop roots: The recommended air temperature is 20–21° Centigrade.
Crop time: Approximately 10 weeks to 2 months are needed to produce a 15-centimeter container from a rooted cutting.
Growth habit: Compact, low growing and slightly spreading.
Suggested container size: 15-centimeter container.
Use: Ornamental for use as a landscape plant or container plant.
Type: Herbaceous perennial.
Height of plant at maturity: 350 mm. in height.
Width of plant at maturity: 450 mm. in width.
Cultural requirements: Grow in full sun with moderate water, and well-draining soil such as loam.
Resistance to pests and diseases: 'Fanfare' has not been observed to exhibit any resistance to any particular pest or disease. 'Fanfare' is susceptible to downy mildew and to thrips as may be typical of *Gaillardia.*
Hardiness: USDA Zone 5.
Growing requirements: If grown outside in regions which experience winter freezing, 'Fanfare' may be started as a cutting during the spring or summer of the previous year, planted out prior to the onset of winter, and flowering will commence typically in May or June according to the region and season. When grown outside in frost-free regions, or in frost-protected greenhouses, 'Fanfare' will flower virtually all year round and may be started as a cutting (which should be non-flowering) at any time of year.
Stem:
*Branching habit.*—Basal branching.
*Stem color.*—138C.
*Stem dimensions.*—9–12 cm in length and 5 mm. in width.
*Stem shape.*—Cylindrical.
*Stem surface.*—The surface is villous and fluted.
*Internode length.*—Average internode length is 2 cm.
Foliage:
*Type.*—Evergreen.
*Leaf arrangement.*—Alternate.
*Leaf form.*—Undivided, simple.
*Margin.*—Entire.
*Leaf shape.*—Oblanceolate.
*Leaf length.*—11 cm. in length.
*Leaf width.*—2 cm. in width.
*Leaf base.*—Atteuate.
*Leaf apex.*—Rounded.
*Leaf venation pattern.*—Parallel. Mid vein protrudes on both adaxial and abaxial surfaces.
*Vein color* (*abaxial surfaces*).—138D.
*Vein color* (*adaxial surfaces*).—138D.
*Leaf surface* (*abaxial surface*).—Pubescent.
*Leaf surface* (*adaxial surface*).—Pubescent.
*Color of pubescence* (*adaxial and abaxial surface*).—156D.
*Leaf attachment.*—Sessile.
*Presence of stipules or spines.*—None.
*Leaf color* (*adaxial surface*).—138A.
*Leaf color* (*abaxial surface*).—138B.
*Fragrance.*—A slight sage-like scent has been observed.
Inflorescence:
*Inflorescence.*—Solitary.
*Aspect.*—Facing upward.
*Dimensions of inflorescence.*—60–70 mm. in diameter and 30 mm. in length.
*Inflorescence type.*—Radiate capitate.
*Inflorescence shape.*—Radiate with center disc.
*Inflorescence number per plant.*—Very numerous: a mature one-year old plant may bear approximately 100 inflorescences in bud and flower at one time.
*Blooming season.*—Spring, summer and fall.
*Peduncle dimensions.*—7–9 cm in length and 3 mm. in width.
*Peduncle shape.*—Cylindrical.
*Peduncle surface.*—Surface is pubescent and exhibits longitudinal ridges.
*Peduncle color.*—138D.
*Peduncle strength.*—Moderate.

*Immature inflorescence shape* (*bud*).—Closest to rotate whorl.
*Immature inflorescence dimensions* (*bud*).—3 cm. in diameter and 1.50 cm. in length.
*Color of immature inflorescence* (*bud*).—138B.
*Surface of immature inflorescence* (*bud*).—Villous.
*Ray flower shape.*—Tubular.
*Ray flower surface* (*outer surface*).—Pubescent.
*Ray flower surface* (*inner surface*).—Glabrous.
*Ray flower arrangement.*—Radiate.
*Number of ray flowers per inflorescence.*—18 to 25 ray flowers per inflorescence.
*Number of petals per ray flower.*—Four.
*Fused or unfused.*—Petals are basally fused.
*Petal margins of ray flowers.*—Entire.
*Ray flower dimensions.*—3.50 cm. in length, 1.50 cm. in width at the widest end, 0.50 cm. in width at the corolla tube, and 15 mm. in depth.
*Color of ray flower petals* (*outer and inner surfaces*).—17A.
*Color of ray flower corolla tube* (*outer surface*).—42B.
*Color of ray flower corolla tube* (*inner surface*).—40A or brighter, with darker longitudinal veins 42A.
*Self-cleaning or persistent.*—Self-cleaning.
*Quantity of disc florets per inflorescence.*—Approximately 75–150 disc florets per inflorescence.
*Disc floret dimensions* (*including pistil length*).—12 mm. in length and 3 mm. in width.
*Depth of disc floret corolla tube.*—9 mm. in depth.
*Surface of disc florets.*—Lanate.
*Disc floret color.*—183A.
*Number of receptacular bracts* (*chaff*).—Variable.
*Dimensions of receptacular bract* (*chaff*).—6 mm. in length and 0.25 mm. in width.
*Color of receptacular bract* (*chaff*).—156D.
*Phyllary dimensions.*—5.50 cm. in diameter and 3 cm. in length.
*Phyllary color.*—147B.
*Phyllary arrangement.*—Whorl.
*Number of involucral bracts.*—An average of 25 in number per inflorescence.
*Shape of involucral bract.*—Closest to oblanceolate.
*Involucral bract dimensions.*—2 cm. in length and 0.50 cm. in width.
*Involucral bract margin.*—Entire.
*Involucral bract apex.*—Acute.
*Involucral bract base.*—Truncate.
*Involucral bract color* (*adaxial surface*).—147B.
*Involucral bract color* (*abaxial surface*).—147B.
*Involucral bract surface* (*abaxial surface*).—Pubescent.
*Involucral bract surface* (*adaxial surface*).—Pubescent.
*Fragrance of inflorescence.*—Sweet fragrance.

Reproductive organs:
*Stamens.*—Present and adnate to inner surface of corolla tube of disc florets.
*Number of stamens.*—Three stamens present.
*Stamen dimensions.*—20 cm. in width and 5 mm. in length.
*Stamen color.*—17A.
*Stamen form.*—Plumose.
*Anther dimensions.*—0.50 mm. in length and 1 mm. in width.
*Anther color.*—187A.
*Anther shape.*—Narrow lanceolate.
*Pollen.*—Present.
*Quantity of pollen.*—Large amount.
*Pollen color.*—17A.
*Pistil.*—One present.
*Pistil length.*—12 mm. in length.
*Style dimensions.*—2 mm. in length and 1 mm. in width.
*Style color.*—150D.
*Stigma dimensions.*—8 mm. in length and 1.75 mm. in width.
*Stigma form.*—Plumose.
*Stigma color.*—187A.
*Stigma shape.*—Bifurcate.
*Ovary position.*—Inferior.
*Ovary color.*—150D.
*Ovary shape.*—Globose.
*Ovary dimensions.*—1 mm. in width and 2 mm in height.

Seed:
*Number of seeds.*—80–90 seeds in number per inflorescence.
*Seed color.*—199D.
*Seed surface.*—Bristled.
*Bristle color.*—156A.
*Seed shape.*—Piriform.
*Seed dimensions.*—1 mm. in length and 0.50 mm. in width.
*Seed surface.*—Papyraceous.

It is claimed:

1. A new and distinct cultivar of *Gaillardia×grandiflora* plant named 'Fanfare' as described and illustrated.

* * * * *